United States Patent [19]

Press et al.

[11] Patent Number: 4,791,200

[45] Date of Patent: Dec. 13, 1988

[54] 2-SUBSTITUTED-4-ARYL-SUBSTITUTED THIAZOLES

[75] Inventors: Jeffery B. Press, Rocky Hill; Pauline Sanfilippo, Flemington; Maud Urbanski, Belle Mead, all of N.J.

[73] Assignee: Ortho Pharmaceutical Corporation, Raritan, N.J.

[21] Appl. No.: 64,717

[22] Filed: Jun. 22, 1987

[51] Int. Cl.$^4$ ............... C07D 277/28; C07D 417/12; A61K 31/425

[52] U.S. Cl. .................... 544/369; 546/209; 546/275; 548/193; 548/195; 548/197; 548/203

[58] Field of Search ............ 548/203, 197, 193, 195; 546/275, 209; 544/369

[56] References Cited

FOREIGN PATENT DOCUMENTS 225129  7/1985  German Democratic Rep. ................................ 548/205

*Primary Examiner*—Robert Gerstl
*Attorney, Agent, or Firm*—Benjamin F. Lambert

[57] ABSTRACT

The present invention relates to novel 2-substituted-4-aryloxyalkylamine thiazoles as described herein. The thiazoles are useful as antisecretory agents.

13 Claims, No Drawings

2-SUBSTITUTED-4-ARYL-SUBSTITUTED THIAZOLES

BACKGROUND OF THE INVENTION

1. Field of the invention

The present invention relates to novel 2-substituted-4-aryloxyalkylamine thiazoles as described further below. The thiazoles are useful as antisecretory agents.

2. Description of the Prior Art

Several 4-aryl-substituted thiazoles have been described which have various biological activities. For example, published European Patent Application No. 130,077 describes a compound having the formula

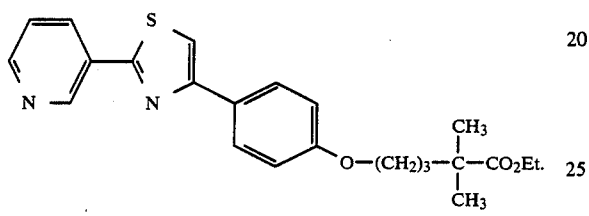

This compound inhibits blood platelet aggregation and demonstrates anti-cholesteremic activity.

Published European Patent Application 117,082 discloses compounds of the formula

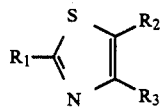

where $R_1$ is OH or $NHCH_3$ and $R_2$ is $CH_3$, $CO_2C_2H_5$, CN or $HC=CHCO_2CH_3$. These compounds exhibit cardiotonic activity.

Derwent Abstract 85-1051681/18 describes compounds of the formula

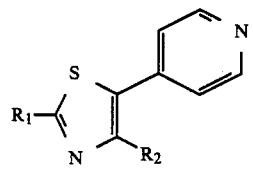

where $R_1$ is cycloalkyl, cyclic amino, lower alkylamino or substituted phenyl, $R_2$ is substituted pyridyl and $R_3$ is phenyl or phenyl substituted by lower alkyl or alkoxy. These compounds have analgesic, antiulcer or blood platelet aggregating activity.

None of the 4-aryl-substituted thiazoles of the prior art discussed above contain a 4-aryloxyalkylamine substituent.

SUMMARY OF THE INVENTION

The present invention is directed to thiazole compounds of the formula

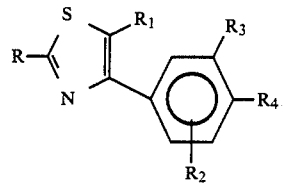

where

R may be $C_1$-$C_4$ alkyl, phenyl, phenyl substituted by $CF_3$, halo such as I, Br, Cl, $C_1$-$C_3$ alkyl or $C_1$-$C_3$ alkoxy, acetamido, nitro, cyano, alkylamino or dialkylamino having 1-4 carbons, or pyridinyl, $R_1$ may be H or $C_1$-$C_4$ alkyl, $R_2$ may be H, $C_1$-$C_4$ alkyl, $C_1$-$C_3$ alkoxy or, Cl, Br, I, $R_3$ or $R_4$ may be $-O-(CH_2)_m-NR_5R_6$, wherein one of $R_3$ or $R_4$ is H, provided that when $R_4$ is $-O-(CH_2)_m-NR_5R_6$, $R_3$ may be hydrogen $C_1$-$C_4$ alkyl, $C_1$-$C_3$ alkoxy, Cl, Br or I, $R_5$ and $R_6$ may be the same or different and may be $C_1$-$C_5$ alkyl, $C_3$-$C_6$ cycloalkyl, benzyl, benzyl substituted by $C_1$-$C_3$ alkyl, $C_1$-$C_3$ alkoxy, halo such as Br, I, Cl or $CF_3$, or $R_5$ and $R_6$ together with N may be imidazole, triazole, piperidine, pyrrolidine or N-substituted piperazine wherein the substituent may be $C_1$-$C_4$ alkyl, phenyl or phenyl substituted by $C_1$-$C_3$ alkoxy, and m may be 2-6, and acid addition salts such as hydrochloride or hydrobromide.

The compounds of formula I are useful as antisecretory agents, such as antiulcer agents.

DETAILED DESCRIPTION OF THE INVENTION

The invention in its broadest aspects relates to thiazole compounds which have antisecretory activity. The thiazole compounds of the invention demonstrating an antisecretory activity are shown by formula I above. The thiazole compounds contain a substituent at the 2-position of the thiazole ring and an aryloxyalkylamine substituent at the 4-position.

The preferred compounds of the present invention are those wherein R is phenyl or substituted phenyl, $R_1$ is H, $R_2$ is H, $R_4$ is $-O(CH_2)_m-NR_5R_6$ and m is 2-5.

The compounds of formula I can be prepared as shown in Scheme 1.

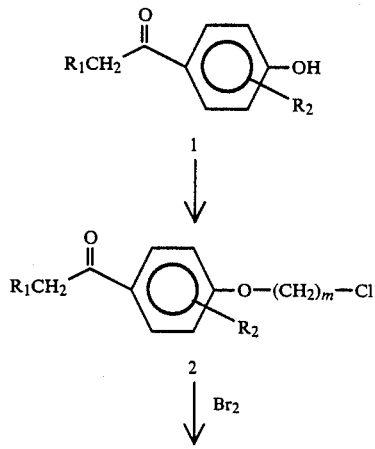

SCHEME 1

-continued
SCHEME 1

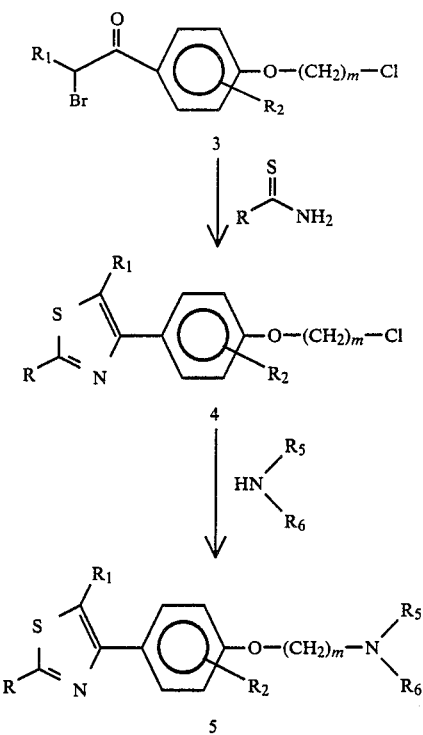

The p-hydroxyphenyl-n-alkyl ketone 1, such as p-hydroxyacetophenone, p-hydroxypropriophenone or p-hydroxybutyrophenone, is treated with a 1-bromo-ω-chloroalkane in a refluxing alcoholic base for 12–48 hours to produce the p-chloroalkoxyphenone 2. Chloroalkanes which can be utilized include 1-bromo-2-chloroethane, 1-bromo-3-chloropropane, 1-bromo-4-chlorobutane, 1-bromo-5-chloropentane or 1-bromo-6-chlorohexane. Methanolic potassium hydroxide is a suitable alcoholic base. The p-chloroalkoxyphenone 2 is reacted with bromine in glacial acetic acid, carbon disulfide or an ether solvent at 10°–65° C. for 2–24 hours to produce the α-bromoketone 3. Suitable ethers include tetrahydrofuran, diethylether or dimethoxyether.

The α-bromoketone 3 is condensed with a thioamide in an alcoholic solvent at 65°–85° C. for 2–24 hours to yield the chloroalkoxyphenylthiazole 4. Suitable alcohols include methanol, ethanol and isopropanol. Thioamides which can be utilized include thioacetamide, thiobenzamide, 4-chlorothiobenzamide, 4-methoxythiobenzamide, 3,5-dimethoxythiobenzamide, 4-methylthiobenzamide, thionicotinamide or thioisonicotinamide. The chloroalkoxyphenylthiazole 4 is converted to the 4-aryloxyalkylamine-thiazole 5 by treatment with an amine as the solvent neat or in an inert solvent at 100°–150° C. for 4–72 hours. Suitable inert solvents include benzene, toluene, 2-methoxyethylether or diglyme. Amine solvents which can be utilized include dimethylamine, diethylamine, dipropylamine, dibutylamine, dipentylamine, benzylamine, benzylmethylamine, or cyclic amines such as piperidine, pyrrolidine, imidazole, triazole, N-methylpiperazine or 4-(2-methoxyphenyl)piperazine.

Alternatively, a m-hydroxyphenyl-n-alkyl ketone can be used in place of the p-hydroxyphenyl-n-alkyl ketone 1 to produce the corresponding 4-aryl-substituted thiazoles in which the oxyalkylamine substituent is in the meta-position relative to the thiazole ring.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain dosage unit, e.g., tablet, capsule, powder, injection, teaspoonful and the like, from about 1 to about 100 mg/kg, and preferably from about 5 to about 25 mg/kg of the active ingredient.

The following examples describe the invention in greater particularity and are intended to be a way of illustrating but not limiting the invention.

EXAMPLE 1

4-(4-Dibutylaminopropoxyphenyl)-2-phenylthiazole

To a mixture of p-hydroxyacetophenone (50.7 g, 0.37 mol) and 1-bromo-3-chloropropane (160 ml, 1.5 mol) in methanol (250 ml) was added portionwise potassium hydroxide (63 g, 1.12 mol). The mixture was stirred at reflux for 24 hours, cooled to room temperature, filtered through Celite and evaporated in vacuo. The residual semisolid was diluted with diethyl ether (500 ml) and washed with $H_2O$ (2×300 ml). The ether solution was dried over $MgSO_4$, filtered and evaporated in vacuo to give p-chloropropoxyphenone as a liquid in 68% yield (53.3 g). $^1H$ NMR ($CDCl_3$): δ7.98–7.89 (d, J=8.9 Hz, 2H), 7.02–6.92 (d, J=8.9 Hz, 2H), 4.16 (t, J=5.9 Hz, 2H), 3.75 (t, J=6.4 Hz, 2H), 2.52 (s, 3H), 2.34–2.16 (m, 2H).

To a stirred solution of the p-chloropropoxyphenone (53.3 g, 0.25 mol) in diethyl ether (250 ml) was slowly added bromine (13 ml, 0.25 mol) and allowed to stir at room temperature for 16 hours. The dark mixture was poured into an aqueous saturated sodium bicarbonate solution (300 ml) and the organic layer separated. The ether layer was washed with an aqueous saturated sodium bicarbonate solution (300 ml) and with water (300 ml) and dried over $MgSO_4$. The solution was filtered and evaporated in vacuo to yield the α-bromoketone intermediate (64.4 g, 88% yield) as a dark oil. $^1H$ NMR ($CDCl_3$): δ7.96 (d, J=8.9 Hz, 2H), 6.95 (d, J=8.9 Hz, 2H), 4.41 (s, 2H), 4.19 (t, 2H), 3.75 (t, 2H), 2.26 (m, 2H).

A mixture of the α-bromoketone (26 g, 89 mmol) and thiobenzamide (12 g, 89 mmol) in ethanol (150 ml) was stirred at reflux for three hours, cooled to room temperature and filtered to give the p-chloropropoxyphenylthiazole (17.6 g, 56% yield) as a brown solid, mp 72°–75° C. IR(KBr): 1610 cm$^{-1}$, MS: 330(M+). $^1$H NMR (CDCl$_3$): δ7.95 (m, 4H), 7.33 (m, 4H), 6.98 (d, J=8 Hz, 2H), 4.17 (t, J=5.9 Hz, 2H), 3.78 (t, J=5.9 Hz, 2H), 2.25 (m, 2H).

Theor. C$_{18}$H$_{16}$NOSCl: C, 65.54; H, 4.89; N, 4.25; Found: C, 64.86; H, 4.80; N, 4.19.

A suspension of the p-chloropropoxyphenylthiazole (5.6 g, 17.1 mmol) in dibutylamine (60 ml) was stirred at 120° C. for five hours. The excess dibutylamine was removed by distillation and the resulting oil was flash-chromatographed (SiGel, 9:1 CH$_2$Cl$_2$—MeOH) to give the free base of the title compound as an oil. The HCl salt was prepared by dropwise addition of concentrated hydrochloric acid to a solution of the free base in methanol, concentrated and recrystallized from acetone to yield the named compound (2.58 g, 75% yield) as an off-white solid, mp 131°–134° C. IR(KBr): 2030, 1615 cm$^{-1}$, MS: 422(M+). $^1$H NMR (CD$_3$OD): δ8.00–7.57 (m, 8H), 7.14–7.05 (m, 2H), 4.20 (t, J=5.8 Hz, 2H), 3.21 (m, 6H), 2.28 (m, 2H), 1.85–1.34 (m, 8H), 1.01 (m, 6H).

Theor. C$_{26}$H$_{34}$N$_2$OS.HCl: C, 68.02; H, 7.68; N, 6.10; Found: C, 67.44; H, 7.59; N, 5.87.

EXAMPLE 2

4-(4-Dibutylaminopropoxyphenyl)-2-methylthiazole

The title compound was prepared as described in Example 1 using thioacetamide in place of the thiobenzamide (0.70 g, 9.3 mmol) to produce 0.45 g (16% yield) of the free base of the title compound which was converted to the HCl salt, mp 120°–122° C. IR(KBr): 3440, 2930 cm$^{-1}$, MS: 360(M+). $^1$H NMR (CD$_3$OD): δ7.94 (s, 1H), 7.79 (d, J=9.0 Hz, 2H), 7.15 (d, J=9.0 Hz, 2H), 4.21 (t, J=6 Hz, 2H), 3.33–3.12 (m, 6H), 3.01 (s, 3H), 2.23 (m, 2H), 1.90–1.27 (m, 8H), 1.01 (m, 6H).

Theor. C$_{21}$H$_{32}$N$_2$OS.2HCl: C, 58.19; H, 7.91; N, 6.46; Found: C, 58.18; H, 7.96; N, 6.38.

EXAMPLE 3

4-(4-Dibutylaminopropoxyphenyl)-5-methyl-2-phenylthiazole

The named compound was prepared as described in Example 1 using α-bromo-4-(chloropropoxy)propiophenone (10 g, 44 mmol) as the α-bromoketone intermediate and 6.0 g (45 mmol) thiobenzamide to produce 6.75 g (73% yield) of the free base of the named compound which was converted to the HCl salt, mp 102°–104° C. IR(KBr): 3410, 2610, 1615 cm$^{-1}$, MS: 437(M+). $^1$H NMR (CD$_3$OD): δ8.04–7.95 (m, 2H), 7.79–7.60 (m, 5H), 7.18 (d, J=8.0 Hz, 2H), 4.23 (t, J=5.7 Hz, 2H), 3.40–3.14 (m, 6H), 2.56 (s, 3H), 2.28 (m, 3H), 1.90–1.35 (m, 8H), 1.02 (m, 6H).

Theor. C$_{27}$H$_{36}$N$_2$OS.2HCl.½H$_2$O: C, 62.53; H, 7.58; N, 5.40; Found: C, 62.70; H, 7.60; N, 5.36.

EXAMPLE 4

4-(4-Diethylaminopropoxyphenyl)-2-phenylthiazole

The procedure of Example 1 was followed using 1.2 g (8.9 mmol) thiobenzamide and using diethylamine in place of dibutylamine to produce 1.33 g (40% yield) of the free base of the title compound which was converted to the HCl salt, mp 156°–158° C. IR(KBr): 3440, 2610, 1620 cm$^{-1}$, MS: 367(M−). $^1$H NMR (CD$_3$OD): δ8.00–7.97 (m, 4H), 7.67 (s, 1H), 7.51–7.45 (m, 3H), 7.02 (d, J=8.7 Hz, 2H), 4.15 (t, J=5 Hz, 2H), 3.40–3.09 (m, 6H), 2.24 (m, 2H), 1.88–1.30 (m, 8H), 1.01 (m, 6H).

Theor. C$_{22}$H$_{26}$N$_2$OS.HCl.H$_2$O: C, 62.76; H, 6.94; N, 6.66; Found: C, 63.22; H, 6.72; N, 6.69.

EXAMPLE 5

4-(4-Dipropylaminopropoxyphenyl)-2-phenylthiazole

The title compound was prepared as described in Example 1 using 2.3 g (17 mmol) thiobenzamide and using dipropylamine in place of dibutylamine to produce 3.0 g (48% yield) of the free base of the title compound which was converted to the HCl salt, mp 154°–156° C. IR(KBr): 3440, 2410, 1610 cm$^{-1}$, MS: 395(MH+). $^1$H NMR (CD$_3$OD): δ8.00–7.91 (m, 4H), 7.70 (s, 1H), 7.52–7.46 (m, 3H), 7.09–6.99 (m, 2H), 4.17 (t, J=6 Hz, 2H), 3.47–3.08 (m, 6H), 2.21 (m, 2H), 1.83 (m, 4H), 1.03 (m, 6H).

Theor. C$_{24}$H$_{30}$N$_2$OS.HCl.½H$_2$O: C, 65.50; H, 7.33; N, 6.36; Found: C, 65.87; H, 7.33; N, 6.37.

EXAMPLE 6

4-[4-(4-Methylpiperazol-1-yl)propoxyphenyl]-2-phenylthiazole

The procedure of Example 1 was followed with thiobenzamide (5.0 g, 37 mmol) and using N-methylpiperazine in place of dibutylamine to produce 3.4 g (23% yield) of the free base of the title compound which was converted to the HCl salt, mp >240° C. IR(KBr): 3440, 2360, 1620 cm$^{-1}$, MS: 394(MH+). $^1$H NMR (CD$_3$OD): δ8.15–7.80 (m, 10H), 4.15 (m, 10H), 3.55 (m, 5H), 2.22 (m, 2H).

Theor. C$_{23}$H$_{27}$N$_3$OS.2HCl.½H$_2$O: C, 58.09; H, 6.36; N, 8.84; Found: C, 58.51; H, 6.20; N, 8.89.

EXAMPLE 7

4-[4-[4-(2-Methoxyphenyl)piperazol-1-yl]propoxyphenyl]-2-phenylthiazole

The named compound was prepared according to Example 1 with thiobenzamide (5.0 g, 37 mmol) and using 4-(2-methoxyphenyl)piperazine in place of dibutylamine to produce 2.7 g (25% yield) of the free base of the named compound which was converted to the HCl salt, mp 218°–220° C. IR(KBr): 3420, 2380, 1610 cm$^{-1}$, MS: 486(MH+). $^1$H NMR (CD$_3$OD): δ8.09–7.02 (m, 14H), 4.22 (t, J=5.9 Hz, 2H), 3.93 (s, 3H), 3.62 (m, 10H), 2.37 (m, 2H).

Theor. C$_{29}$H$_{31}$N$_3$O$_2$S.2HCl.½H$_2$O: C, 61.36; H, 6.04; N, 7.40; Found: C, 61.80; H, 6.38; N, 7.48.

EXAMPLE 8

4-[4-(3-Piperidino)propoxyphenyl]-2-phenylthiazole

The procedure of Example 1 was followed with thiobenzamide (3.2 g, 24 mmol) and using piperidine in place of dibutylamine to produce 2.9 g (38% yield) of the free base of the title compound which was converted to the HCl salt, mp 218°–221° C. IR(KBr): 2520, 1620 cm$^{-1}$, MS: 379(MH+). $^1$H NMR (CD$_3$OD): δ8.03–7.91 (m, 4H), 7.66 (s, 1H), 7.47 (m, 3H), 7.01 (d, J=8.0 Hz, 2H), 4.16 (t, J=5.7 Hz, 2H), 3.38–3.22 (m, 6H), 2.27 (m, 2H), 1.87 (m, 6H).

Theor. C$_{23}$H$_{26}$N$_2$OS.HCl: C, 66.56; H, 6.56; N, 6.75; Found: C, 66.07; H, 6.54; N, 6.62.

EXAMPLE 9

4-[4-(3-Pyrrolidino)propoxyphenyl]-2-phenylthiazole

The title compound was prepared according to Example 1 with thiobenzamide (1.3 g, 9.0 mmol) and using pyrrolidine in place of dibutylamine to produce 1.5 g (46% yield) of the free base of the title compound which was converted to the HCl salt, mp 214°–217° C. IR(KBr): 2490, 1615 cm$^{-1}$, MS: 365(MH+). $^1$H NMR (CD$_3$OD): δ8.07–7.91 (m, 4H), 7.66 (s, 1H), 7.51–7.44 (m, 3H), 7.02 (d, J=8.9 Hz, 2H), 4.09 (t, J=5.8 Hz, 2H), 3.42 (m, 6H), 2.17 (m, 6H).

Theor. C$_{22}$H$_{24}$N$_2$OS.HCl: C, 65.89; H, 6.28; N, 6.99; Found: C, 65.52; H, 6.39; N, 6.85.

EXAMPLE 10

4-[4-(1H-Imidazol-1-yl)propoxyphenyl]-2-phenylthiazole

Following the procedure of Example 1 the named compound was prepared with thiobenzamide (1.1 g, 8.2 mmol) and using imidazole in place of dibutylamine to produce 2.0 g (67% yield) of the free base of the named compound which was converted to the HCl salt, mp 173°–177° C. IR(KBr): 3400, 1610 cm$^{-1}$, MS: 362(MH+). $^1$H NMR (CD$_3$OD): δ9.04 (m, 1H), 8.03–7.53 (m, 10H), 7.02 (d, J=8.9 Hz, 2H), 4.46 (t, J=6.8 Hz, 2H), 4.09 (t, J=5.6 Hz, 2H), 2.43 (m, 2H).

Theor. C$_{21}$H$_{19}$N$_3$OS.HCl.H$_2$O: C, 60.63; H, 5.33; N, 10.10; Found: C, 60.93; H, 5.02; N, 10.17.

EXAMPLE 11

4-(4-Benzylmethylaminopropoxyphenyl)-2-phenylthiazole

The title compound was prepared as described in Example 1 with thiobenzamide (1.7 g, 13 mmol) and using benzylmethylamine in place of dibutylamine to produce 4.0 g (74% yield) of the free base of the title compound which was converted to the HCl salt, mp 189°–192° C. IR(KBr): 2490, 1620 cm$^{-1}$, MS: 415(MH+). $^1$H NMR (CD$_3$OD): δ7.98–7.89 (m, 4H), 7.51 (s, 1H), 7.46–7.43 (m, 8H), 6.98 (d, J=8.7 Hz, 2H), 4.38 (s, 2H), 4.11 (t, J=5.7 Hz, 2H), 3.45–3.37 (m, 2H), 2.84 (s, 3H), 2.29 (m, 2H).

Theor. C$_{26}$H$_{26}$N$_2$OS.HCl: C, 69.23; H, 6.04; N, 6.21; Found: C, 68.77; H, 5.97; N, 6.12.

EXAMPLE 12

4-(4-Dibutylaminoethoxyphenyl)-2-phenylthiazole

The procedure of Example 1 was followed with p-hydroxyacetophenone (2.0 g, 15 mmol) and using 1-bromo-2-chloroethane (7.4 ml, 89 mmol) in place of 1-bromo-3-chloropropane to give 2.2 g (74% yield) of 4-chloroethoxyacetophenone. $^1$H NMR (CDCl$_3$): δ7.93 (d, J=8.9 Hz, 2H), 6.97 (d, J=8.9 Hz, 2H), 4.22 (t, J=5.6 Hz, 2H), 3.82 (t, J=3.8 Hz, 2H), 2.53 (s, 3H). Bromination (3.4 ml, 66 mmol) of this product (2.2 g, 66 mmol) followed by condensation with thiobenzamide (1.5 g, 11 mmol) as described in Example 1 gave 4-(4-chloroethoxyphenyl)-2-phenylthiazole (2.6 g, 89% yield). $^1$H NMR (CDCl$_3$): δ8.04–7.88 (m, 4H), 7.47–7.31 (m, 4H), 6.96 (d, J=8.9 Hz, 2H), 4.25 (t, J=5.6 Hz, 2H), 3.82 (t, J=3.8 Hz, 2H). Treatment of this product (3.6 g, 11 mmol) with dibutylamine in accordance with Example 1 afforded 1.5 g (30% yield) of the free base of the title compound which was converted to the HCl salt, mp 129°–131° C. IR(KBr): 2400, 1610 cm$^{-1}$, MS: 409(MH+). $^1$H NMR (CD$_3$OD): δ8.10–7.98 (m, 4H), 7.73 (s, 1H), 7.50 (m, 3H), 7.12 (d, J=8.7 Hz, 2H), 4.45 (t, J=5.0 Hz, 2H), 3.67 (t, J=4.9 Hz, 2H), 3.31 (m, 4H), 1.79–1.34 (m, 8H), 1.04 (m, 6H).

Theor. C$_{25}$H$_{32}$N$_2$OS.HCl: C, 67.46; H, 7.47; N, 6.30; Found: C, 67.15; H, 7.78; N, 6.26.

EXAMPLE 13

4-(4-Dibutylaminobutoxyphenyl)-2-phenylthiazole

The title compound was prepared in accordance with Example 1 with p-hydroxyacetophenone (33 g, 0.24 mol) and using 1-bromo-4-chlorobutane (50 ml, 0.43 mol) in place of 1-bromo-3-chloropropane to give 51 g (66% yield) of 4-chlorobutoxyacetophenone. $^1$H NMR (CDCl$_3$): δ7.92 (d, J=8.0 Hz, 2H), 6.92 (d, J=8.0 Hz, 2H), 4.04 (m, 2H), 3.56 (m, 2H), 2.55 (s, 3H), 1.98 (m, 4H). Bromination (46 g, 0.20 mol) of this product (51 g, 0.16 mol) followed by condensation with thiobenzamide (4.5 g, 33 mmol) as described in Example 1 gave 4-(4-chlorobutoxyphenyl)-2-phenylthiazole (9.0 g, 64% yield) as a yellow solid, mp 154°–156° C. Treatment of this product (7.2 g, 21 mmol) with dibutylamine in accordance with Example 1 afforded 6.8 g (74% yield) of the free base of the title compound which was converted to the HCl salt, mp 132°–134° C. IR(KBr): 2440, 1615 cm$^{-1}$, MS: 437(MH+). $^1$H NMR (CD$_3$OD): δ7.97–7.88 (m, 4H), 7.74 (s, 1H), 7.55–7.48 (m, 3H), 7.03 (d, J=8.0 Hz, 2H), 4.10 (m, 2H), 3.21–3.06 (m, 6H), 1.92–1.23 (m, 12H), 0.98 (m, 6H).

Theor. C$_{27}$H$_{36}$N$_2$OS.HCl: C, 68.54; H, 7.88; N, 5.92; Found: C, 68.51; H, 8.18; N, 5.89.

EXAMPLE 14

4-[4-(1H-Imidazol-1-yl)butoxyphenyl]-2-phenylthiazole

The title compound was prepared as described in Example 13, starting with 4-(4-chlorobutoxyphenyl)-2-phenylthiazole (7.8 g, 18 mmol) and using imidazole (3.8 g, 55 mmol) in place of dibutylamine to produce 3.6 g (53% yield) of the free base of the title compound which was converted to the HCl salt, mp 178°–180° C. IR(KBr): 3500, 2720, 1615 cm$^{-1}$, MS: 376(MH+). $^1$H NMR (CD$_3$OD): δ9.00 (s, 1H), 8.03–6.96 (m, 12H), 4.38 (t, J=6.0 Hz, 2H), 4.09 (t, J=6.0 Hz, 2H), 2.22–1.79 (m, 4H).

Theor. C$_{22}$H$_{21}$N$_3$OS.HCl.½H$_2$O: C, 62.77; H, 5.51; N, 9.98; Found: C, 62.83; H, 5.33; N, 9.98.

EXAMPLE 15

4-(4-Dibutylaminopentoxyphenyl)-2-phenylthiazole

The title compound was prepared according to Example 1, with p-hydroxyacetophenone (9.0 g, 66 mmol) and using 1-bromo-5-chloropentane (25 g, 0.13 mol) in place of 1-bromo-3-chloropropane to give 16 g (100% yield) of 4-chloropentoxyacetophenone. $^1$H NMR (CDCl$_3$): δ7.92 (d, J=9.0 Hz, 2H), 6.91 (d, J=9.0 Hz, 2H), 4.03 (t, J=5.9 Hz, 2H), 3.54 (m, 2H), 2.55 (s, 3H), 1.85–1.52 (m, 6H). Bromination (11 g, 66 mmol) followed by condensation with thiobenzamide (3.8 g, 28 mmol) of this product as described in Example 1 gave 4-(4-chloropentoxyphenyl)-2-phenylthiazole (8.5 g, 69% yield) as a yellow solid, mp 158°–160° C. $^1$H NMR (CD$_3$OD): δ8.02–7.62 (m, 8H), 7.04 (d, J=9.0 Hz, 2H), 4.04 (t, J=5.0 Hz, 2H), 3.59 (t, J=6.0 Hz, 2H), 1.79 (m, 6H). Treatment of this product (8.5 g, 25 mmol) with dibutylamine in accordance with Example 1 afforded 5.1 g (58% yield) of the free base of the title compound which was converted to the HCl salt, mp 88°–90° C.

IR(KBr): 3500, 2660, 1610 cm$^{-1}$, MS: 451(MH+). $^1$H NMR (CDCl$_3$): δ7.97–7.45 (m, 8H), 6.94 (d, J=8.0 Hz, 2H), 4.02 (t, J=5.6 Hz, 2H), 2.98 (m, 6H), 1.95–1.22 (m, 14H), 0.96 (m, 6H).

Theor. C$_{28}$H$_{38}$N$_2$OS.HCl.H$_2$O: C, 66.57; H, 8.18; N, 5.55; Found: C, 66.83; H, 8.09; N, 5.56.

EXAMPLE 16

4-(4-(Dibutylaminopropoxyphenyl)-2-(4-chlorophenyl)thiazole

The procedure of Example 1 was followed, using 4-chlorothiobenzamide (7.0 g, 41 mmol) in place of thiobenzamide to produce 6.4 g (34% yield) of the free base of the named compound which was converted to the HCl salt, mp 150°–152° C. IR(KBr): 2400, 1610 cm$^{-1}$, MS: 457(MH+). $^1$H NMR (CD$_3$OD): δ7.96 (m, 4H), 7.69 (s, 1H), 7.48 (d, J=8.6 Hz, 2H), 7.02 (d, J=8.6 Hz, 2H), 4.20 (t, J=5.5 Hz, 2H), 3.48–3.11 (m, 6H), 2.21 (m, 2H), 1.72–1.33 (m, 8H), 1.01 (m, 6H).

Theor. C$_{26}$H$_{33}$ClN$_2$OS.HCl: C, 63.27; H, 6.94; N, 5.68; Found: C, 63.44; H, 7.22; N, 5.70.

EXAMPLE 17

4-(4-Dibutylaminopropoxyphenyl)-2-(4-methoxyphenyl)thiazole

The title compound was prepared in accordance with Example 1, using 4-methoxythiobenzamide (5.0 g, 30 mmol) in place of thiobenzamide to produce 4.5 g (33% yield) of the free base of the title compound which was converted to the HCl salt, mp 67°–70° C. IR(KBr): 3400, 2720, 1615 cm$^{-1}$, MS: 453(MH+). $^1$H NMR (CD$_3$OD): δ7.91–7.20 (m, 9H), 4.21 (t, J=5.5 Hz, 2H), 3.92 (s, 3H), 3.38–3.13 (m, 6H), 2.25 (m, 6H), 1.76–1.33 (m, 8H), 1.01 (m, 6H).

Theor. C$_{27}$H$_{36}$N$_2$O$_2$S.2HCl.½H$_2$O: C, 60.66; H, 7.35; N, 5.24; Found: C, 60.41; H, 7.36; N, 5.23.

EXAMPLE 18

4-(4-Dibutylaminopropoxyphenyl)-2-(3,5-dimethoxyphenyl)thiazole

The procedure of Example 1 was followed, using 3,5-dimethoxythiobenzamide (5.1 g, 26 mmol) in place of thiobenzamide to produce 3.8 g (30% yield) of the free base of the title compound which was converted to the HCl salt, mp 139°–143° C. IR(KBr): 3480, 2500, 1615 cm$^{-1}$, MS: 483(MH+). $^1$H NMR (CD$_3$OD): δ7.88–6.69 (m, 8H), 4.20 (m, 2H), 3.87 (s, 6H), 3.45–3.18 (m, 6H), 2.25 (m, 2H), 1.90–1.34 (m, 8H), 1.01 (m, 6H).

Theor. C$_{28}$H$_{38}$N$_2$O$_3$S.HCl.H$_2$O: C, 62.60; H, 7.69; N, 5.22; Found: C, 66.12; H, 7.45; N, 5.15.

EXAMPLE 19

4-(4-Dibutylaminopropoxyphenyl)-2-(4-methylphenyl)thiazole

The title compound was prepared according to Example 1 using 4-methylthiobenzamide (2.6 g, 17 mmol) in place of thiobenzamide to produce 3.3 g, (44% yield) of the free base of the title compound which was converted to the HCl salt, mp 144°–147° C. IR(KBr): 2500, 1615 cm$^{-1}$, MS: 437(MH+). $^1$H NMR (CD$_3$OD): δ7.95 (m, 5H), 7.38 (d, J=8.2 Hz, 2H), 7.08 (d, J=8.8 Hz, 2H), 4.19 (t, J=5.6 Hz, 2H), 3.41–3.12 (m, 6H), 2.43 (s, 3H), 2.29 (m, 2H), 1.75–1.33 (m, 8H), 1.01 (m, 6H).

Theor. C$_{27}$H$_{36}$N$_2$OS.2HCl: C, 63.63; H, 7.52; N, 5.50; Found: C, 64.23; H, 7.57; N, 5.68.

EXAMPLE 20

4-(4-Dibutylaminopropoxyphenyl)-2-(4-trifluoromethylphenyl)thiazole

In accordance with Example 1, 4-trifluoromethylthiobenzamide (3.8 g, 18.3 mmol) was used in place of thiobenzamide to produce 2.1 g (24% yield) of the free base of the named compound which was converted to the HCl salt, mp 148°–150° C. IR(KBr): 1620 cm$^{-1}$, MS: 491(MH+).

Theor. C$_{27}$H$_{33}$F$_3$N$_2$OS.HCl.H$_2$O: C, 59.49; H, 6.68; N, 5.14; Found: C, 59.14; H, 6.32; N, 5.20.

EXAMPLE 21

4-(4-Dibutylaminopropoxyphenyl)-2-(3-pyridinyl)thiazole

The title compound was prepared according to Example 1 using thionicotinamide (3.3 g, 24 mmol) in place of thiobenzamide to produce 3.7 g (36% yield) of the free base of the title compound which was converted to the HCl salt, mp 199°–202° C. IR(KBr): 3500, 2620, 1615 cm$^{-1}$, MS: 424(MH+). $^1$H NMR (CD$_3$OD): δ9.53 (s, 1H) 9.17 (d, J=8.2 Hz, 1H), 8.91 (d, J=5.4 Hz, 1H), 8.14 (m, 4H), 7.06 (d, J=8.8 Hz, 2H), 4.20 (t, J=5.7 Hz, 2H), 3.39–3.13 (m, 6H), 2.29 (m, 2H), 1.75–1.29 (m, 8H), 1.01 (m, 6H).

Theor. C$_{25}$H$_{33}$N$_3$OS.2HCl.2H$_2$O: C, 58.35; H, 7.25; N, 8.17; Found: C, 58.52; H, 7.42; N, 8.20.

EXAMPLE 22

4-[3,5-Dichloro-4-(dibutylaminopropoxy)phenyl]-2-phenylthiazole

Following the procedure of Example 1, 3,5-dichloro-4-hydroxyacetophenone (10 g, 49 mmol) was used in place of p-hydroxyacetophenone with 1-bromo-3-chloropropane (21 ml, 0.20 mol) to give 10.5 g (76% yield) of 3,5-dichloro-4-chloropropoxyacetophenone. $^1$H NMR (CDCl$_3$): δ7.88 (s, 2H), 4.24 (t, J=5.7 Hz, 2H), 3.86 (t, J=6.4 Hz, 2H), 2.57 (s, 3H), 2.24 (m, 2H). Bromination (6.0 g, 37 mmol) followed by condensation with thiobenzamide (2.6 g, 19 mmol) of this product in accordance with Example 1 afforded 4-[3,5-dichloro-4-(chloropropoxy)phenyl]-2-phenylthiazole in 98% yield (7.4 g). $^1$H NMR (CD$_3$OD): δ8.08–7.48 (m, 8H), 4.22 (t, J=5.7 Hz, 2H), 3.89 (t, J=6.4 Hz, 2H), 2.32 (m, 2H). Treatment of this product (3.9 g, 9.8 mmol) with dibutylamine in accordance with Example 1 gave 2.5 g (48% yield) of the free base of the title compound which was converted to the HCl salt, mp 167°–169° C. IR(KBr): 2440 cm$^{-1}$, MS: 491(MH+). $^1$H NMR (CD$_3$OD): 8.05–7.46 (m, 8H), 4.20 (t, J=5.0 Hz, 2H), 3.64–3.16 (m, 6H), 2.28 (m, 2H), 1.85–1.34 (m, 8H), 1.01 (m, 6H).

Theor. C$_{26}$H$_{32}$Cl$_2$N$_2$OS.HCl: C, 59.14; H, 6.30; N, 5.31; Found: C, 58.84; H, 6.40; N, 5.25.

EXAMPLE 23

4-[3,5-Dichloro-4-(1H-imidazol-1-yl)propoxyphenyl]-2-phenylthiazole

The title compound was prepared as described in Example 22 using 4-[3,5-dichloro-4-(chloropropoxy)phenyl]-2-phenylthiazole (4.2 g, 11 mmol) and imidazole (2.2 g, 33 mmol) in place of dibutylamine to give 1.9 g (40% yield) of the free base of the title compound which was converted to the HCl salt, mp 204°–207° C. IR(KBr): 3400, 2540 cm$^{-1}$, MS: 430(MH+). $^1$H NMR (CD$_3$OD): δ9.08 (brs, 1H), 8.03–7.48 (m, 10H), 4.65 (t, J=5.0 Hz, 2H), 4.12 (t, J=4.5 Hz, 2H), 2.50 (m, 2H).

Theor. C$_{21}$H$_{17}$Cl$_2$N$_3$OS.HCl: C, 54.03; H, 3.89; N, 9.00; Found: C, 53.98; H, 3.85; N, 8.92.

EXAMPLE 24

4-[4-(1,2,4-Triazol-1-yl)propoxyphenyl]-2-phenylthiazole

The procedure of Example 1 was followed, using 4-chloropropoxyphenylthiazole (4.1 g, 12.4 mmol) and triazole (2.5 g, 37 mmol) in place of dibutylamine to give 1.6 g (37% yield) of the free base of the named compound which was converted to the HCl salt, mp 197°–198° C. IR(KBr): 1620 cm$^{-1}$, MS: 363(MH+). $^1$H NMR (CD$_3$OD): δ9.73 (s, 1H), 8.80 (s, 1H), 8.02–7.86 (m, 5H), 7.67 (s, 1H), 7.50 (m, 2H), 6.95 (d, J=8.9 Hz, 2H), 4.66 (t, J=6.7 Hz, 2H), 4.13 (t, J=5.8 Hz, 2H), 2.46 (m, 2H).

Theor. C$_{20}$H$_{18}$N$_4$OS.HCl: C, 60.21; H, 4.80; N, 14.05; Found: C, 60.77; H, 4.80; N, 14.12.

EXAMPLE 25

5-Ethyl-4-(4-dibutylaminopropoxyphenyl)-2-phenylthiazole

The title compound was prepared according to Example 1, using p-hydroxybutyrophenone (20 g, 0.12 mol) in place of p-hydroxyacetophenone and 1-bromo-3-chloropropane (48 ml, 0.48 mol) to give 25 g (85% yield) of p-chloropropoxybutyrophenone as an oil. $^1$H NMR (CDCl$_3$): δ7.92 (d, J=8.9 Hz, 2H), 6.91 (d, J=8.9 Hz, 2H), 4.15 (t, J=5.9 Hz, 2H), 3.73 (t, J=6.3 Hz, 2H), 2.87 (t, J=7.0 Hz, 2H), 2.23 (m, 2H), 1.78 (m, 2H), 0.99 (t, J= 7.0 Hz, 3H). Bromination (5 ml, 0.10 mol) followed by condensation with thiobenzamide (10 g, 73 mmol) of this product as described in Example 1 afforded 5-ethyl-4-(4-chloropropoxyphenyl)-2-phenylthiazole in 48% yield (15 g) as a white solid, mp 117°–119° C. Treatment of this product (5.1 g, 11 mmol) with dibutylamine in accordance with Example 1 gave 4.4 g (83% yield) of the free base of the title compound which was converted to the HCl salt, mp 128°–131° C. IR(KBr): 3400, 2610, 1620 cm$^{-1}$, MS: 451(MH+). $^1$H NMR (CD$_3$OD): δ7.96–7.02 (m, 9H), 4.12 (t, J=5.8 Hz, 2H), 3.38–2.76 (m, 8H), 2.20 (m, 2H), 1.75–1.18 (m, 14H), 0.91 (m, 3H).

Theor. C$_{28}$H$_{38}$N$_2$OS.HCl.3/2H$_2$O: C, 65.40; H, 8.23; N, 5.45; Found: C, 65.42; H, 7.88; N, 5.48.

EXAMPLE 26

4-[3-Methyl-4-dibutylaminopropoxy)phenyl]-2-phenylthiazole

The title compound was prepared as described in Example 1, using 3-methyl-4-hydroxyacetophenone (10 g, 67 mmol) in place of p-hydroxyacetophenone and 1-chloro-3-bromopropane (42 g, 0.27 mol) to give 3-methyl-4-chloropropoxyacetophenone (13 g, 86% yield) as an amber oil. $^1$H NMR (CDCl$_3$): δ7.78 (m, 2H), 6.85 (m, 1H), 4.18 (t, J=5.8 Hz, 2H), 3.77 (t, J=6.2 Hz, 2H), 2.54 (s, 3H), 2.23 (m, 5H). Bromination (4 ml, 78 mmol) of this product (13 g, 58 mmol) as described in Example 1 followed by condensation with thiobenzamide (7.6 g, 56 mmol) afforded 4-[3-methyl-4-chloropropoxy)phenyl]-2-phenylthiazole in 95% yield (22 g). $^1$H NMR (CD$_3$OD): δ8.05–7.56 (m, 9H), 4.19 (t, J=5.9 Hz, 2H), 3.81 (t, J=6.4 Hz, 2H), 3.31 (m, 5H). Reaction of this product (4.0 g, 11.6 mmol) with dibutylamine in accordance with Example 1 afforded 2.9 g (57% yield) of the free base of the title compound which was converted to the HCl salt, mp 141°–143° C. IR(KBr): 3360, 2600, 1600 cm$^{-1}$, MS: 437(MH+). $^1$H NMR (CD$_3$OD): δ8.05–6.98 (m, 9H), 4.18 (t, J=6 Hz, 2H), 3.55–3.18 (m, 6H), 2.35 (m, 5H), 1.90–1.31 (m, 8H), 1.02 (m, 6H).

Theor. C$_{27}$H$_{36}$N$_2$OS.2HCl.3/2H$_2$O: C, 60.43; H, 7.70; N, 5.22; Found: C, 60.16; H, 7.54; N, 5.04.

EXAMPLE 27

4-[3-(1H-Imidazol-1-yl)propoxyphenyl]-2-phenylthiazole

The named compound was prepared according to Example 1 using m-hydroxyacetophenone (15 g, 0.11 mol) in place of p-hydroxyacetophenone and 1-chloro-3-bromopropane (33 ml, 0.33 mol) to give 3-chloropropoxyacetophenone (17 g, 73% yield) as an amber oil. $^1$H NMR (CDCl$_3$): δ7.59–7.07 (m, 4H), 4.18 (t, J=6 Hz, 2H), 3.77 (t, J=6 Hz, 2H), 2.60 (s, 3H), 2.25 (m, 2H). Bromination (3.6 ml, 71 mmol) of this product (15 g, 71 mmol) followed by condensation with thiobenzamide (6.8 g, 49 mmol) as described in Example 1 afforded 4-[3-chloropropoxyphenyl]-2-phenylthiazole (14 g, 88% yield) as an oil. $^1$H NMR (CD$_3$OD): δ8.09–6.98 (m, 10H), 4.21 (t, J=6 Hz, 2H), 3.79 (t, J=6 Hz, 2H), 2.24 (m, 2H). Treatment of this product (10 g, 30 mmol) in accordance with Example 1, with imidazole in place of dibutylamine, gave 4.1 g (38% yield) of the named compound as an amber oil. IR(KBr): 3360, 1600 cm$^{-1}$, MS: 362(MH+). $^1$H NMR (CDCl$_3$): δ8.10–6.85 (m, 13H), 4.22 (t, J=5.8 Hz, 2H), 4.01 (t, J=5.7 Hz, 2H), 2.26 (m, 2H).

Theor. C$_{21}$H$_{19}$N$_3$OS.½H$_2$O: C, 68.08; H, 5.44; N, 11.34; Found: C, 67.79; H, 5.44; N, 10.95.

By substituting m-hydroxyacetophenone for the p-hydroxyacetophenone, p-hydroxypropiophenone or p-hydroxybutyrophenone of Examples 1–26, the corresponding 4-(3-aminoalkoxyphenyl)-2-substituted thiazoles are produced. For example, 4-(3-dibutylaminopropoxyphenyl)-2-phenylthiazole, 4-[3-(4-methylpiperazol-1-yl)propoxyphenyl]-2-phenylthiazole and 2-(4-chlorophenyl)-4-(3-dibutylaminopropoxyphenyl)-thiazole are produced by using m-hydroxyacetophenone in Examples 1, 6 and 16, respectively.

Additional 4-aryloxyalkylamine thiazoles are produced in accordance with any of the preceding examples by using the following amines in place of the amines utilized in the preceding examples to treat the chloroalkoxyphenylthiazoles: dibenzylamine, cyclohexylamine, dicyclohexylamine, propylamine, cyclopropylamine, N-methylbutylamine, N-methylcyclohexylamine, 4-methylbenzylamine, 4-methoxybenzylamine and 4-chlorobenzylamine.

Anti-Secretory Activity

Gastro-duodenal ulcerations are produced and maintained by excess secretion of gastric acid. The predominant source of this acid is found in the parietal cells whose exocrine secretion in the stomach is almost pure hydrochloric acid (Am. J. Gastro. 77, 281 (1982)). The parietal cells are stimulated to secrete acid by such substances as gastrin, acetylcholine and histamine. (Drugs, 26, 439 (1983)). Inhibition of parietal cell secretion via an antihistamine, anticolinergic, anti-gastrin or via inhibition of internal mechanisms of the parietal cells either singularly or in combination provides a useful treatment for ulcers.

The anti-secretory activity of representative compounds was examined by employing three different assays, as more fully described in Examples 28–30.

EXAMPLE 28

Isolated Parietal Cell Assay

The isolated parietal cell assay was conducted using the procedures of Batzri, S. et al., *Biochemica et Biophysica Acta* 508, 328 (1978) and Soll, A. H. *Am. J. Physiol.* 238, G366 (1980). Basically, parietal cells were isolated from the fundic mucosa of rabbit stomachs by a four-stage collagenase digestion process. The supernatant fractions from the last two stages of this process contain the individual parietal cells. This cell suspension was centrifuged and reconstituted in a modified Hank's buffer to contain $1$–$2 \times 10^6$ cells/ml. The cells in this suspension were then evaluated for their ability to accumulate $^{14}$C-aminopyrine ($^{14}$C-AP), a weak base which has been shown to accumulate in acidic environments such as the parietal cell. This accumulation was stimulated by histamine and was blocked by $H_2$ antagonists. The cells were incubated with $0.4$–$0.5 \times 10^6$ cpm $^{14}$C-AP, with various concentrations of histamine as a stimulant, $1 \times 10^{-5}$M isobutylmethylxanthine, and the test compound added in a 20 $\mu$l volume of buffer or DMSO. The flasks were incubated in a shaking water bath at 37° C. for 20 minutes. Two aliquots were then taken from each flask and cell pellets were collected by centrifugation. The pellets were solubilized with Protosol (New England Nuclear) and radioactivity determined by liquid scintillation spectrometry. Data is presented as the IC$_{50}$ vhist, the concentration of compound required to inhibit $^{14}$C-AP accumulation in the histamine stimulated parietal cell by 50%. The results are shown in Table I.

When dibutyryl cAMP was used to stimulate the cells instead of histamine, a similar inhibition of $^{14}$C-AP accumulation was measured and the data are presented as the IC$_{50}$ vcAMP, the concentration required to inhibit $^{14}$C-AP accumulation in the cAMP stimulated parietal cell by 50%.

EXAMPLE 29

Inhibition of Parietal Cell H+K+ATPase

The inhibition of parietal cell H+K+ATPase was determined in fundic mucosa from New Zealand white rabbits which were homogenized in a modified Tris buffer consisting of 250 mM sucrose, 0.2 mM EDTA and 5.0 mM Tris adjusted to pH 7.4 with HCl. The activity was measured in a 1 ml incubation volume containing 50 mM Tris pH 7.4, 2 mM MgCl$_2$, 2 mM Na$_2$ATP, with or without 20 mM KCl and vehicle control (dimethylsulfoxide) or test compound added in a 0.02 ml volume. Typically, 20–50 $\mu$g membrane protein was added and the tubes were preincubated with test compound for 10 minutes at 37° C. Substrate, Na$_2$ATP, was then added and the tubes were incubated for another 15 minutes at 37° C. The reaction was stopped by the addition of 1 ml 14% trichloroacetic acid and the samples were centrifuged at 2,000 $\times$g for 10 minutes. The amount of inorganic phosphate present in an aliquot of supernatant was determined. H+K+ATPase activity was determined after correcting for the basal (Mg++ only) enzyme activity present in the membrane preparation. The amount of inhibition of the ATPase is shown in Table I.

EXAMPLE 30

Gastric Secretion

The inhibitory activity of the compounds on acid output was tested using pylorus ligation in a modification of the procedure of Shay, H. et al., *Gastroenterology* 26, 906 (1954). Basically, male Charles River Sprague Dawley derived rats weighing 150–300 grams were deprived of food but not water for 18–24 hours prior to use. Water was withheld during the experiment, however. The rats were weighed, anesthetized with ether and the pylorus ligated according to the method of Shay et al., supra. Treatment or vehicle control was then administered intraduodenally (i.d.) or subcutaneously (s.c.). Rats were housed two/cage and sacrificed with CO$_2$ four hours after ligation. The stomachs were removed, rinsed, and contents emptied into a graduated centrifuge tube. The tubes were centrifuged, the volume of gastric juice recorded, and any samples obviously contaminated by feces, food or blood were eliminated. A 1 ml aliquot of gastric juice was titrated with 0.1N NaOH to a pH of 7.0–7.4. The volume of gastric juice secreted, the acid concentration, and the product of the volume times the concentration, i.e., the total amount of acid secreted, were measured. The amount of the acid output by the test compounds compared to the control is shown in Table I.

TABLE I

| Compound (Example) | Example 28 IC$_{50}$($\mu$M) | Example 29 % Inhibition at Concentration | Example 30 % Acid Secreted at mpK |
|---|---|---|---|
| 1 | .45vhist; .42vcAMP | 47% @ $10^{-4}$M | 97% @ 40 75% @ 20 50% @ 17.0 |
| 2 | 1.5vhist; 8.4vcAMP | 22% @ $10^{-4}$M | 8% @ 20 |
| 3 | .27vhist; .23vcAMP | 65% @ $10^{-4}$M | 36% @ 20 |
| 4 | .12vhist; .09vcAMP | 50% @ 47 $\mu$M | 82% @ 40 |
| 5 | .23vhist; .18vcAMP | 60% @ $10^{-4}$M | 94% @ 40 |
| 6 | .18vhist; .12vcAMP | 50% @ 44 $\mu$M | 18% @ 40 |
| 7 | .48vhist; .34vcAMP | 28% @ $10^{-4}$M | — |
| 8 | .11vhist; .05vcAMP | 50% @ 34 $\mu$M | 92% @ 40 46% @ 20 25% @ 10 |
| 9 | .39vhist; <10vcAMP | 50% @ 32 $\mu$M | 36% @ 20 |
| 10 | .08vhist; 0.02vcAMP | 50% @ 18 $\mu$M | 91% @ 20 78% @ 10 50% @ 5.7 33% @ 5 |
| 11 | .37vhist; .21vcAMP | 39% @ $10^{-4}$M | 48% @ 20 |
| 12 | .31vhist; .35vcAMP | 44% @ $10^{-4}$M | 41% @ 20 |
| 13 | .13vhist; .12vcAMP | 64% @ $10^{-4}$M | 90% @ 40 56% @ 20 |
| 14 | .82vhist; .31vcAMP | 0% @ $10^{-4}$M | 31% @ 40 |
| 15 | .49vhist; .86vcAMP | 58% @ $10^{-4}$M | 54% @ 20 |
| 16 | 2.1vhist; 1.8vcAMP | 55% @ $10^{-4}$M | 40% @ 20 |
| 17 | .48vhist; .23vcAMP | 33% @ $10^{-4}$M | 4% @ 20 |
| 18 | .26vhist; .54vcAMP | 30% @ $10^{-4}$M | 17% @ 20 |
| 19 | 1.5vhist; 3.0vcAMP | 50% @ 24 $\mu$M | 41% @ 20 |
| 20 | 2.9vhist; | 50% @ 10.6 $\mu$M | 40% @ 40 |

TABLE I-continued

| Compound (Example) | Example 28 IC$_{50}$(μM) | Example 29 % Inhibition at Concentration | Example 30 % Acid Secreted at mpK |
|---|---|---|---|
| 21 | 2.0vcAMP 1.65vhist; .88vcAMP | 50% @ 20 μM | 19% @ 20 |
| 22 | .58vhist; .24vcAMP | 29% @ 10$^{-4}$M | 41% @ 20 |
| 23 | .40vhist; .46vcAMP | 50% @ 2.4 μM | 33% @ 20 |
| 24 | 10vhist; | 36% @ 10$^{-4}$M | 83% @ 40 |
| 25 | .34vhist; .24vcAMP | 5% @ 10$^{-4}$M | 8% @ 20 |
| 26 | .30vhist; .29vcAMP | 23% @ 10$^{-4}$M | 64% @ 20 |
| 27 | .32vhist; .29vcAMP | 50% @ 10.5 μM | 13% @ 20 |

What is claimed is:

1. A compound of the formula

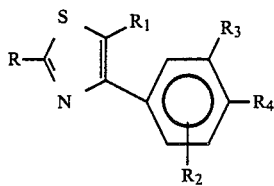

where
R is $C_1$–$C_4$ alkyl, phenyl, phenyl substituted by $CF_3$, halo selected from I, Br, Cl, $C_1$–$C_3$ alkyl or $C_1$–$C_3$ alkoxy, acetamido, nitro, cyano, alkylamino or dialkylamino having 1–4 carbons or pyridinyl,
$R_1$ is H or $C_1$–$C_4$ alkyl,
$R_2$ is H, $C_1$–$C_4$ alkyl, $C_1$–$C_3$ alkoxy Cl, Br, or I,
$R_3$ or $R_4$ are —O—$(CH_2)_m$—$NR_5R_6$, wherein one of $R_3$ or $R_4$ is H, provided that when $R_4$ is —O—$(CH_2)_m$—$NR_5R_6$, $R_3$ is hydrogen, $C_1$–$C_4$ alkyl, $C_1$–$C_3$ alkoxy, or Cl, Br or I,
$R_5$ and $R_6$ are the same or different and are $C_1$–$C_5$ alkyl, $C_3$–$C_6$ cycloalkyl, benzyl, benzyl substituted by $C_1$–$C_3$ alkyl, $C_1$–$C_3$ alkoxy, halo selected from Br, I, Cl or $CF_3$, or $R_5$ and $R_6$ together with N are imidazole, triazole, piperidine, pyrolidine or N-substituted piperazine wherein the substituent is $C_1$–$C_4$ alkyl, phenyl or phenyl substituted by $C_1$–$C_3$ alkoxy, and
m is 2–6, and acid addition salts thereof.

2. A compound of claim 1 wherein $R_3$ is H.
3. A compound of claim 1 wherein $R_4$ is H.
4. A compound of claim 1 wherein $R_1$ is H, $CH_3$ or $C_2H_5$ and $R_2$ is H.
5. A compound of claim 2 wherein $R_1$ is H, $CH_3$ or $C_2H_5$ and $R_2$ is H.
6. A compound of claim 1 wherein $R_5$ and $R_6$ are the same and are a $C_1$–$C_5$ alkyl.
7. A compound of claim 2 wherein $R_5$ and $R_6$ are the same and are a $C_1$–$C_5$ alkyl.
8. A compound of claim 1 wherein $R_5$ and $R_6$ together with the N are imidazole, triazole, piperidine, pyrrolidine or N-substituted piperazine wherein the substituent is $C_1$–$C_4$ alkyl, phenyl or phenyl substituted by $C_1$–$C_3$ alkoxy.
9. A compound of claim 2 wherein $R_5$ and $R_6$ together with the N are imidazole, triazole, piperidine, pyrrolidine or N-substituted piperazine wherein the substituent is $C_1$–$C_4$ alkyl, phenyl or phenyl substituted by $C_1$–$C_3$ alkoxy.
10. A compound of claim 1 selected from the group consisting of 4-(4-dibutylaminopropoxyphenyl)-2-phenylthiazole; 4-(4-dibutylaminopropoxyphenyl)-2-methylthiazole; 4-(4-dibutylaminopropoxyphenyl)-5-methyl-2-phenylthiazole; 4-(4-diethylaminopropoxyphenyl)-2-phenylthiazole; 4-(4-dipropylaminopropoxyphenyl)-2-phenylthiazole; 4-(4-dibutylaminoethoxyphenyl)-2-phenylthiazole; 4-(4-dibutylaminoethoxyphenyl)-2-phenylthiazole; 4-(4-dibutylaminobutoxyphenyl)-2-phenylthiazole; 4-(4-dibutylaminopentoxyphenyl)-2-phenylthiazole; 4-(4-dibutylaminopropoxyphenyl)-2-(4-chlorophenyl)thiazole; 4-(4-dibutylaminopropoxyphenyl)-2-(4-methoxyphenyl)thiazole; 4-(4-dibutylaminopropoxyphenyl)-2-(3,5-dimethoxyphenyl)thiazole; 4-(4-dibutylaminopropoxyphenyl)-2-(4-methylphenyl)thiazole; 4-(4-dibutylaminopropoxyphenyl)-2-(4-trifluoromethylphenyl)thiazole; 4-(4-dibutylaminopropoxyphenyl)-2-(3-pyridinyl)thiazole; 4-[3,5-dichloro-4-(dibutylaminopropoxy)phenyl]-2-phenylthiazole; 5-ethyl-4-(4-dibutylaminopropoxyphenyl)-2-phenylthiazole; and 4-[3-methyl-4-dibutylaminopropoxy)phenyl]-2-phenylthiazole and acid addition salts thereof.
11. A compound of claim 11 which is 4-(4-benzylmethylaminopropoxyphenyl)-2-phenylthiazole and acid addition salts thereof.
12. A compound of claim 1 selected from the group consisting of 4-[4-(4-methylpiperazol-1-yl)propoxyphenyl]-2-phenylthiazole; 4-[4-[4-(2-methoxyphenyl)-piperazol-1-yl]propoxyphenyl]-2-phenylthiazole; 4-[4-(3-piperidino)propoxyphenyl]-2-phenylthiazole; 4-[4-(3-pyrrolidino)propoxyphenyl]-2-phenylthiazole; 4-[4-(1H-imidazol-1-yl)propoxyphenyl]-2-phenylthiazole; 4-[4-(1H-imidazol-1-yl)butoxyphenyl]-2-phenylthiazole; 4-[3,5-dichloro-4-(1H-imidazol-1-yl)propoxyphenyl]-2-phenylthiazole; and 4-[4-(1,2,4-triazol-1-yl)propoxyphenyl]-2-phenylthiazole and acid addition salts thereof.
13. A compound of claim 1 which is 4-[3-(1H-imidazol-1-yl)propoxyphenyl]-2-phenylthiazole and acid addition salts thereof.

* * * * *